(12) United States Patent
Ahmadjian et al.

(10) Patent No.: US 6,958,813 B1
(45) Date of Patent: Oct. 25, 2005

(54) PLUME DETECTOR

(75) Inventors: Mark Ahmadjian, Cambridge, MA (US); Ernest Ray Huppi, Concord, MA (US); Donald R. Smith, W. Newton, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/862,788

(22) Filed: May 18, 2001

Related U.S. Application Data

(60) Provisional application No. 60/206,231, filed on May 22, 2000.

(51) Int. Cl.⁷ ............................................. G01N 21/85
(52) U.S. Cl. ...................... 356/416; 356/311; 356/317; 356/318; 356/336
(58) Field of Search ........................ 356/416, 311, 326, 356/317, 318, 328, 335–343, 438, 574

(56) References Cited

U.S. PATENT DOCUMENTS

| | | | | |
|---|---|---|---|---|
| 5,029,999 A | * | 7/1991 | Kremer et al. ................. | 356/5 |
| 5,220,164 A | * | 6/1993 | Lieber et al. .......... | 250/214 VT |
| 5,479,255 A | * | 12/1995 | Denny et al. ................ | 356/319 |
| 5,546,183 A | * | 8/1996 | Fegley et al. ................ | 356/336 |
| 5,625,452 A | * | 4/1997 | Hasson ....................... | 356/4.07 |
| 5,677,761 A | * | 10/1997 | Hasson ....................... | 356/4.07 |
| 5,686,988 A | * | 11/1997 | Garrett ....................... | 356/318 |
| 5,742,384 A | * | 4/1998 | Farmer ..................... | 356/141.4 |
| 5,850,285 A | * | 12/1998 | Hill, Jr. et al. .............. | 356/311 |
| 6,008,897 A | * | 12/1999 | Sabsabi et al. .............. | 356/318 |
| 6,072,571 A | * | 6/2000 | Houlberg ................ | 356/139.04 |
| 6,118,531 A | * | 9/2000 | Hertel et al. ................. | 356/336 |
| 6,265,704 B1 | * | 7/2001 | Livingston ................ | 250/203.2 |
| 6,373,558 B1 | * | 4/2002 | Hasson ....................... | 356/4.07 |

* cited by examiner

*Primary Examiner*—Ahshik Kim
(74) *Attorney, Agent, or Firm*—Thomas C. Stover

(57) ABSTRACT

Provided is a photodetector that detects missile launches from an above-flying surveillance platform through clouds. The plume detector includes a passive electro-optical sensor which detects the narrow spectral emissions in a rocket engine plume during launch thereof. By detecting a launch upon rocket engine ignition, despite a cloud layer, a gain of up to thirty seconds or more of launch warning is realized and the location of the launch can be accurately determined and the trajectory of such rocket more accurately plotted for enhanced response to such launch. The plume detector of the invention can be carried on a platform such as an aircraft or an orbiting satellite. In each case such detector can spectrally isolate the narrow spectral emissions of interest of a missile or other rocket, as it is launched, for faster tracking and response.

21 Claims, 7 Drawing Sheets

US 6,958,813 B1

PLUME DETECTOR

DOMESTIC PRIORITY

This application claims the benefit of co-pending provisional patent application Ser. No. 60/206,231, filed 22 May 2000.

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to plume detection of vehicles, particularly vehicles being launched or just launched.

2. Description of Related Art

Clouds can limit the effectiveness of conventional sensors, which employ wide band spectral filters. Typical early missile launch warning systems using passive electro-optical sensors do not see through clouds and may not detect a missile launch at the instant of rocket engine ignition if the missile launch area is obscured by clouds. The time from rocket engine ignition to passing through a cloud layer can be thirty seconds or more. This time delay can be vital for applying countermeasures early in the missile flight path and also for accurate location of the missile launch site not only for further countermeasures but to assist in determining the trajectory of such missile.

Prior art references on the subject include "Spectral Analysis of Low Altitude Theatre-class Missile Signatures", Selby et al (U), IRIS Targets, Backgrounds and Discrimination, Monterey, Calif., February 1994, but such references employ wide band spectral filters which have limited ability to see through water vapor or clouds.

There is therefore need and market for a missile launch detector that overcomes the above prior art shortcomings.

There has now been discovered a means for promptly detecting and locating vehicle launches through clouds, fog or haze, well before it passes through, e.g., a cloud layer, a gain of thirty seconds or more in early detection.

SUMMARY OF THE INVENTION

Broadly the present invention provides a rocket plume detector comprising, an electro-optical sensor for detecting narrow band electromagnetic spectral emissions in a rocket engine plume through water vapor, including clouds or fog, during or after a launch thereof, said sensor being mounted on an above-flying or orbiting platform.

Definitions:

By "platform", as used herein, is meant an aircraft or space vehicle.

By "above-flying" as used herein is meant over flying the target vertically or off to one side and looking diagonally down at the target, on the closest approach. Either type of pass is sufficient for plume detection purposes per the invention.

By "narrow spectral band", as used herein, is meant an atomic or molecular emission line or lines detectable by a sensor of the invention.

BRIEF DESCRIPTION OF THE DRAWINGS

The invention will become more apparent from the following detailed specification and drawings in which.

DESCRIPTION OF PREFERRED EMBODIMENTS

A concern of the invention is to provide a sensor or detector able to "see through water" which would offer an advantage in detecting a missile launch from an area obscured by clouds, fog, mist, haze and the like.

Spectral measurements of various solid- and liquid-propellant rocket plumes have shown the presence of strong narrow spectral line emissions from the alkali metals sodium (589.6 nm) and potassium (766.5 nm) in addition to those spectral emissions used by a typical missile warning system. Theoretical calculations indicate that emissions near the 589.6 wavelength should be efficiently transmitted through the atmosphere and clouds and thus should be detectable by a downward-looking sensor positioned above the clouds. The concept is applicable to any spectral emission for which water has transparency. To test this concept, a visible radiometric sensor with a spectral filter (and later with an atomic line resonance filter) was developed and flown on an aircraft platform. In addition, high resolution spectral measurements from an earth orbiting Mid-Course Space Experiment (MSX) satellite were successfully conducted. A ground-based sodium emission source to simulate a rocket engine plume was fabricated using sodium discharge lamps. Aircraft and satellite flight tests were conducted for different cloud types and conditions. These tests demonstrated the feasibility of detecting a missile launch with a narrow spectral sensor over an area obscured by clouds.

Figure 1:
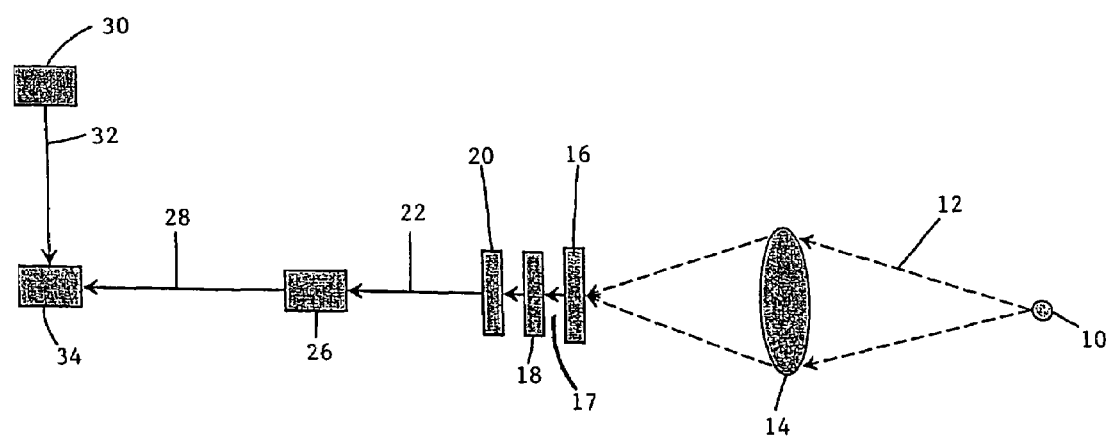
FIG. 1 is a schematic flow chart of the plume detector embodying the present invention.

A narrow spectral band filtered sensor for airborne operation was designed, fabricated, and tested. This sensor, shown schematically in FIG. 1, included a narrow-band filtered photometer 16, 18 & 20, data acquisition electronics 26 and a notebook computer 34 to monitor and record the data.

The photometer had a 50 mm-diameter collecting aperture 14 and a full-angle field of view of 2.0 degrees. A photomultiplier was used as the detector focal plane assembly 18. A 10-nm-wide interference filter 16 centered at 590 nm was used to pass sodium emissions and to reject the background. Typically, the sensor was flown at an altitude of 2000 feet above the cloud tops. At this range the photometer footprint at the cloud tops was about 21 meters.

A lock-in amplifier 20 manufactured by Stanford Laboratories (model SR510) was configured to synchronously rectify the signal from the photometer at twice the 50 Hz reference signal frequency. The analog output of the amplifier was fed to data acquisition electronics 26 where digital samples were taken at a rate of 10 times per second. The sampled digital data was recorded on a data acquisition computer 34. The notebook computer also provided a real-time display of the photometer output. A global positioning system (GPS) receiver 30 recorded the flight path of the aircraft platform for post-flight data analysis.

A ground source 10, to simulate a rocket engine launch, was fabricated using 180-Watt low-pressure sodium discharge lamps. Each bulb was approximately 1 meter long and rated as 33,000 lumens. The bulbs were assembled in pairs with a common reflector element to create 360 W lamps. These lamps were then arranged on the ground in a pattern resembling the spokes of a wheel to create a source with an effective circular diameter of approximately 2 meters. Powered by a 50 Hz generator they produced a modulated output of approximately 26 W/sr.

Figure 2:
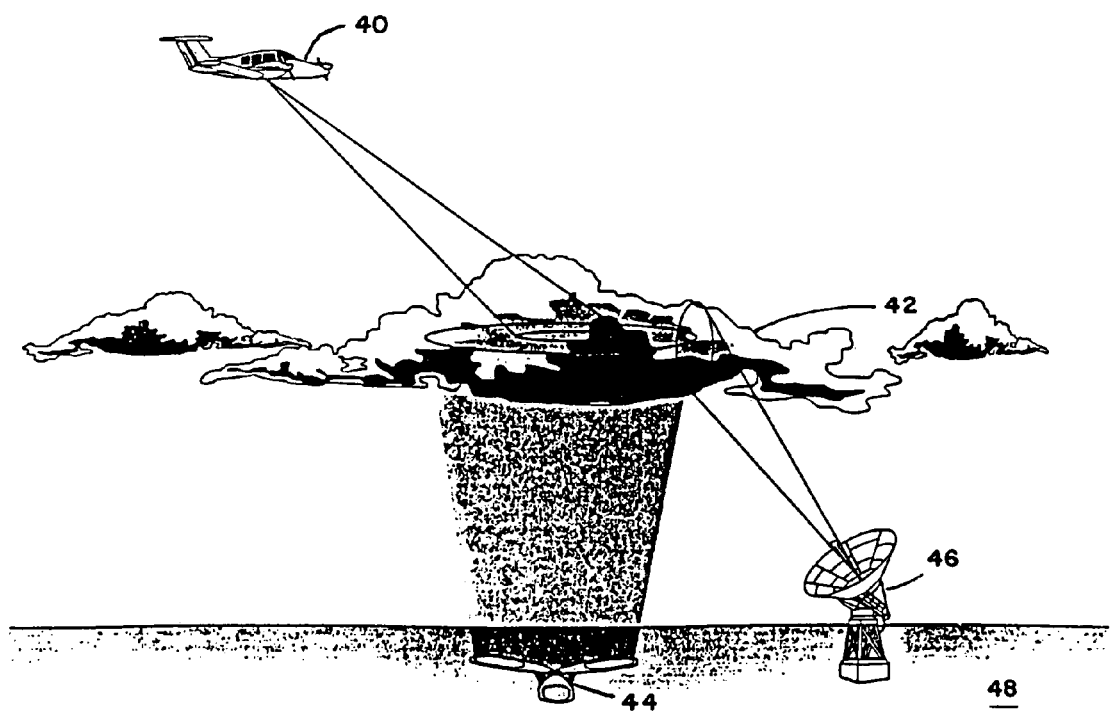
FIG. 2 is fragmentary elevation schematic view of the plume detector of FIG. 1 in use.

The aircraft flight test program was conducted by the Air Force Research Laboratory (AFRL) and measured the diffuse transmission of the sodium ground emission source through clouds and determined the spatial distribution of the scattered radiation at the top of the clouds. The experiment included viewing the cloud tops with an airborne sensor while the clouds were being illuminated from below by the ground-based sodium emission source. The basic experimental concept is illustrated in FIG. 2. An upward pointing radar 46, located near the sodium emission source 44 was used to measure cloud top and bottom altitudes.

The sensor system was mounted in the aft compartment of a twin-engine aircraft 40. The sensor looked out through a window and periscope which were mounted in a compartment door. The periscope contained a mirror at 45 degrees and could be rotated to allow the photometer to view the cloud tops at any desired nadir angle. Most of the data was taken at a nadir angle of zero degrees, but a few measurements were conducted with nadir angles up to 60 degrees. A GPS receiver (not shown), on-board the aircraft. recorded the position of the aircraft as a function of time.

In order to minimize the photon background level, measurements were conducted at night. After the nighttime measurements had been successfully completed, the sensor was modified for daytime operation by replacing the 10-nm-wide interference filter with a much narrower (~0.005 nm) atomic line filter (ALF). The filter incorporates a heated sodium vapor cell with a magnetic field between two crossed polarizers. The crossed polarizers block the background radiation while the signal polarization is rotated by 90 degrees, thus allowing it to pass through the filter. Polarization rotation in the magnetic field is due to the Zeeman effect, which causes a separation in the optical absorption frequencies for right- and left-circularly polarized light. The passband frequency and bandwidth are dependent on temperature and magnetic field and can be adjusted over a relatively wide range. This filter was used in conjunction with a narrow band (0.5 nm) interference filter to help reject background radiation.

Several aircraft data collection flights were conducted. These data flights were flown for two distinctly different "cloud" conditions. The first of these flights measured the transmission of the sodium ground source through a 1000 foot-thick stratus cloud located between 6000 & 7000 ft altitude.

Figure 3:
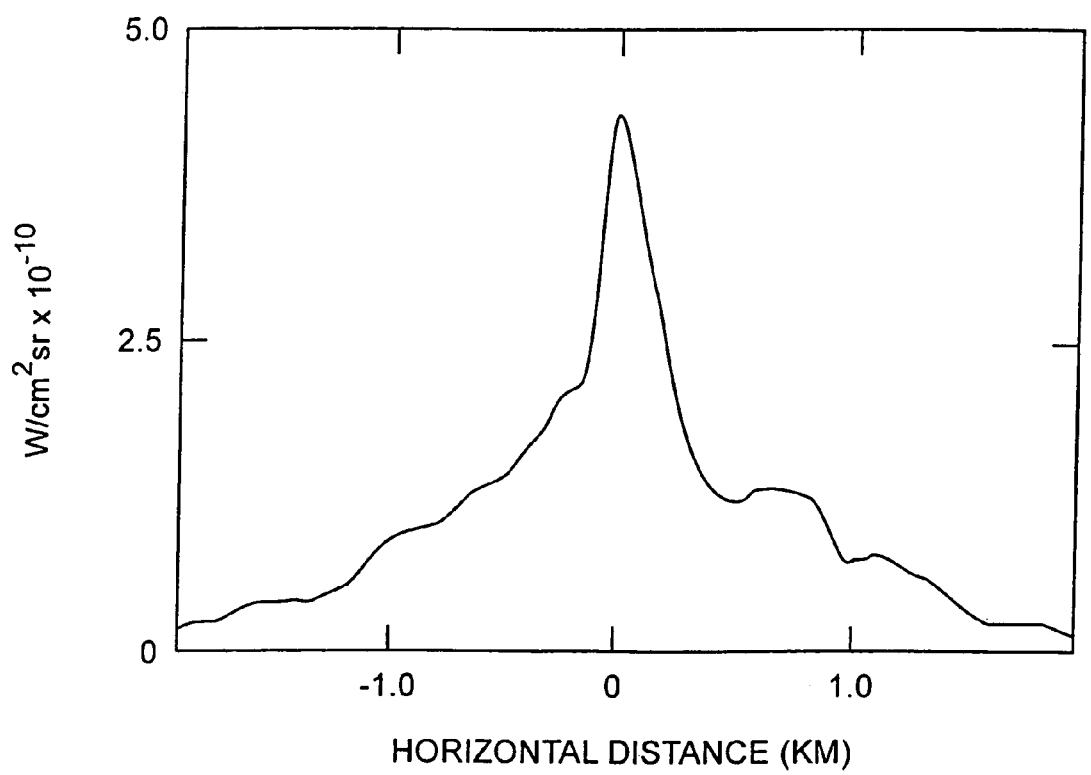
FIGS. 3 and 4 are graphs of detection signals from a plume.
Figure 4:
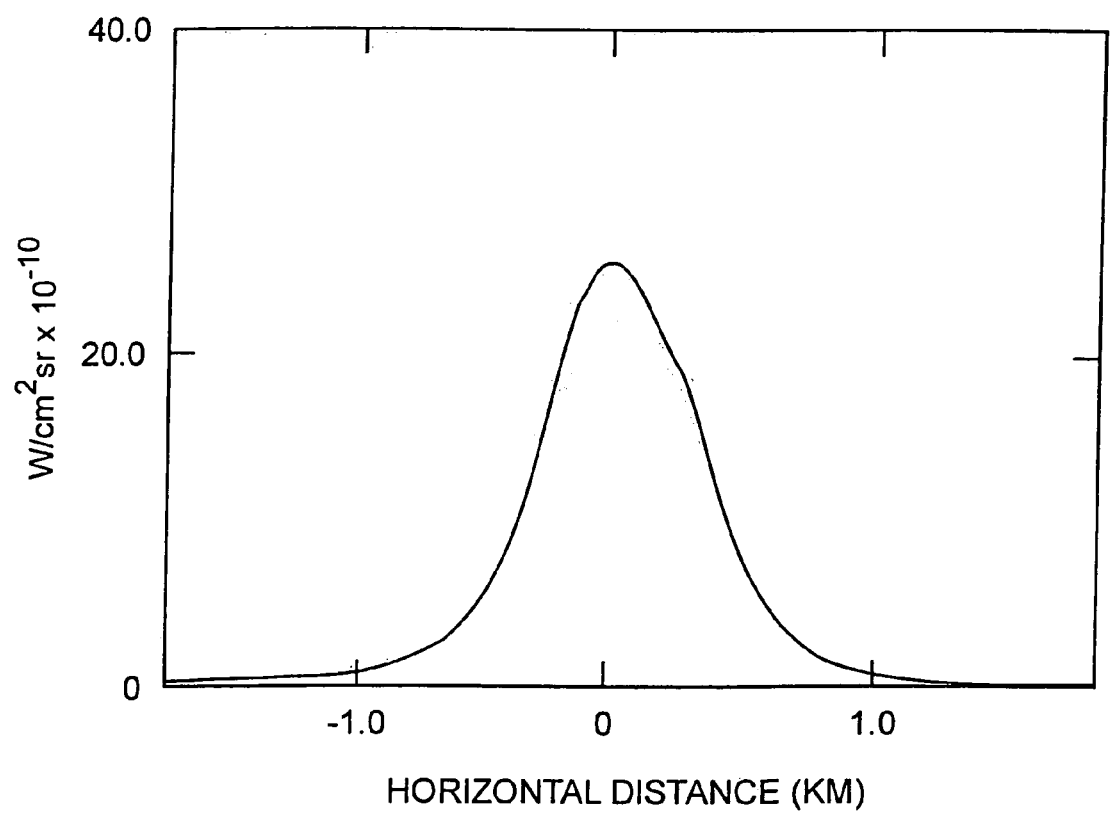

FIG. 3 shows the signal intensity measured through this cloud as a function of horizontal distance. The measured peak radiance was $4.5 \times 10^{-10}$ W/cm$^2$sr and the spatial extent was approximately 3.9 km. One month later, with the aircraft flying at 10,000 feet, the sensor observed the ground source through a much thicker but less dense fog "cloud". This fog layer extended from approximately 1000 to 8000 ft. in altitude and was of a type generally referred to as "radiation fog". This type of fog is characterized by relatively small-diameter droplets (<2 mm). The measured intensity through this fog layer versus horizontal distance in kilometers is shown in FIG. 4. The peak brightness was $2.3 \times 10^{-9}$ W/cm$^2$sr and was measured directly over the target. The spatial extent of the diffused source at the top of the layer was approximately 1.5 km. The noise equivalent (background) radiance (NER) for these measurements was $~1.0 \times 10^{12}$ W/cm$^2$sr, thus yielding S/N ratios in excess of 450.

In both of the above cases, the clouds were visibly opaque. Each of these cloud types was modeled using a Monte Carlo code in order to estimate the extinction coefficients. Based on these simulations, extinction coefficients are estimated to be approximately 9 and 48 km$^{-1}$ for the radiation fog and stratus cloud, respectively. Using these estimates for the extinction coefficients, we have estimated the Liquid Water Content (W) for both cases. These estimated values are W=0.02–0.06 g/m$^3$ and 0.3–0.4 g/m$^3$ for the fog and stratus cloud, respectively.

The detector of the invention was also tested on-board an earth-orbiting MSX satellite. The Ultraviolet and Visible Imagers and Spectrographic Imagers (UVISI) sensor on-board such satellite was used to measure the ground base Na emission source from space. The ground source or sodium lamp assembly effectively served as a point source, as viewed from space, with a radiance of approximately 27 Watts/sr in the sodium doublet at 589 nm. The sodium source was clearly observed by the UVVIS sensor during two overhead passes. In each case the observations were made through a cloud layer.

Figure 5:
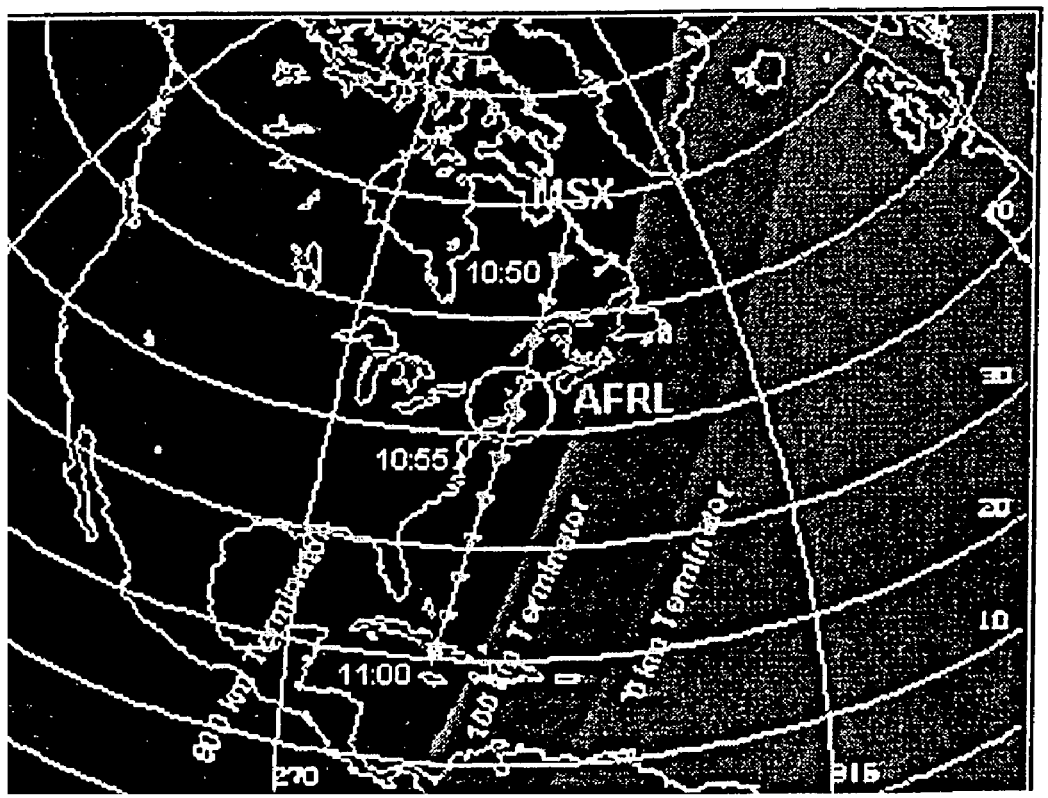
FIG. 5 is a fragmentary schematic plan view showing a satellite platform in orbit.
Figure 6:
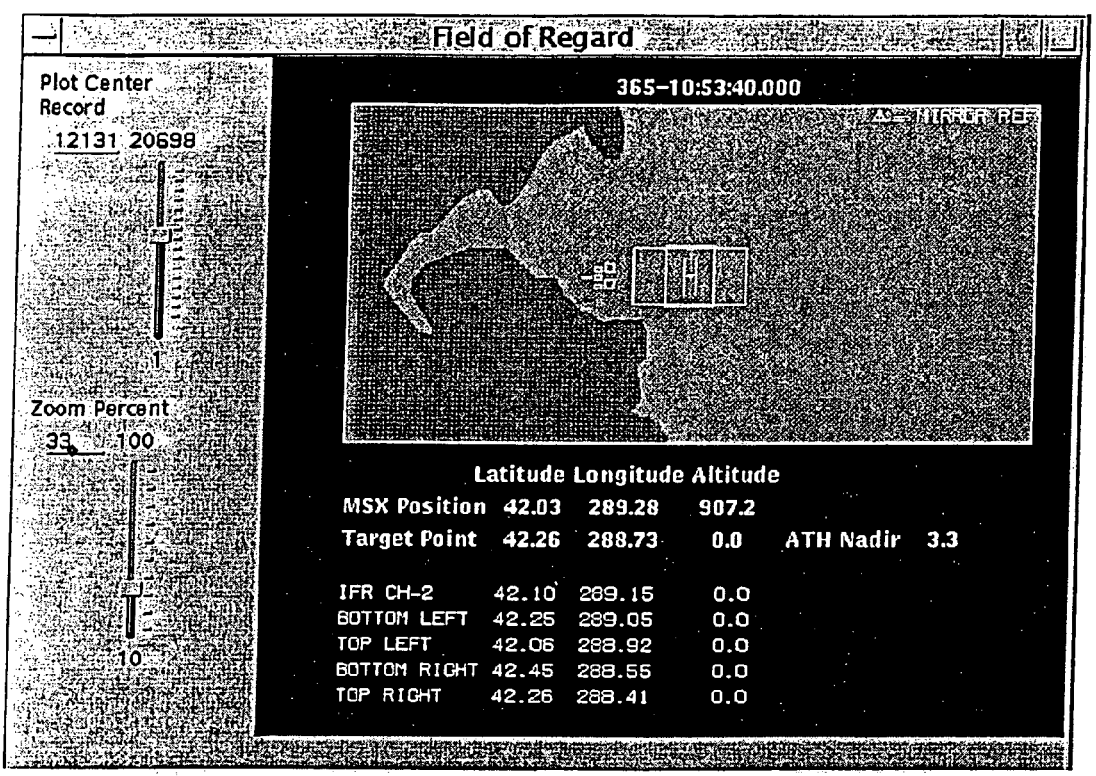
FIG. 6 is a virtual plan view of the satellite sensor's geographic field of view (FOV), looking down on the target through a cloud layer

The satellite track and line of sight of the UVISI instrument is illustrated in FIG. 5 for the experiment performed. This figure also shows the location of the terminators on the ground and at the altitude of the satellite (900 km). The figure shows that although the source on the ground was in darkness, the satellite was sunlit. The attitude control system successfully pointed the line of sight at the ground site at approximately 10:49 UT at a nadir angle of 57 degrees, maintained pointing through closest approach with a nadir angle of 3.6 degrees at 10:53:40.7 UT and continued observation of the ground site stare until 11:00 UT with a nadir angle of 60 degrees as the site approached and then disappeared beyond the horizon. The location and footprints of the FOV's for the various UVISI sensors are shown in FIG. 6 along with a map showing the outline of the observable landmasses.

Figure 7:
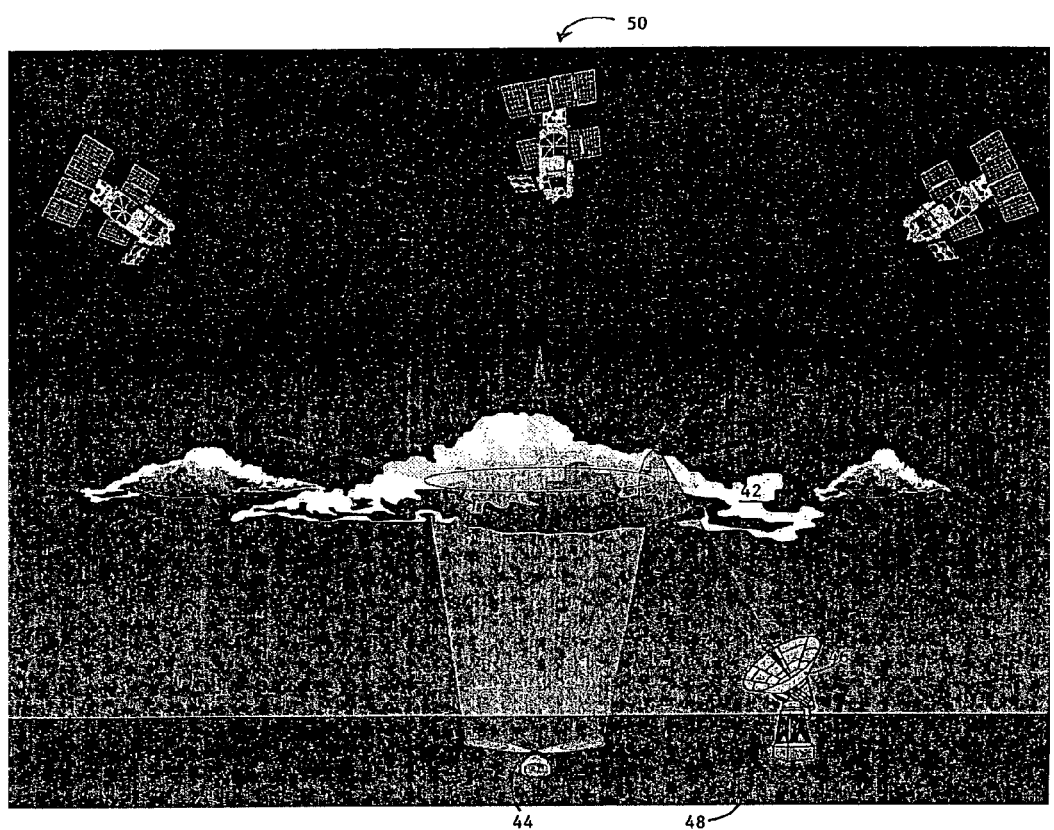
FIG. 7 is a time-lapse elevation schematic of the plume detector embodying the invention in orbit over a simulated rocket plume on the ground.

On both nights there was considerable cloud cover when the observations to place. The thickness of these cloud layers was measured with an upward pointing radar 46, per FIG. 7, which operated at a frequency of 35 GHz (0.86 cm). This radar was located near the source and was turned-on approximately 30 minutes prior to the start of sodium lamp modulation. Table 1 gives the cloud top and bottom altitudes and the average cloud thickness for the two measurement periods, as the satellite 50 passes above. The data confirmed that substantial cloud layers were present on both evenings. The cloud thickness for the first day was nearly twice as thick as that observed during the second day with a much greater optical opacity.

TABLE 1

Summary of cloud data for the two MSX sodium lamp experiments.

| Cloud Thickness (km) | Cloud-bottom Altitude (km) | Cloud-top Altitude (km) |
|---|---|---|
| 1.22 | 0.4 | 1.6 |
| 0.63 | 2.3 | 3.0 |

These aircraft and satellite measurements confirm that a narrow spectral line from a simulated rocket engine plume is detectable through clouds.

In summary, spectral measurements of various solid- and liquid-propellant rocket plumes have shown the presence of strong emissions from sodium (589.6 nm) and potassium (766.5 nm). Theoretical calculations indicated that emissions near 589.6 nm should be efficiently transmitted through the atmosphere and clouds and should be detectable by a downward-looking sensor positioned above the clouds. To test this concept, as described above, a sensor with a narrow spectral band filters was developed and flown on an aircraft platform against a ground-based sodium emission source. In addition, as noted above, a sensor on-board an earth orbiting satellite successfully detected the source emission. These measurements have confirmed that a simulated rocket emission source with a narrow spectral line is detectable through clouds.

The detector of the present invention is readily adapted to a wide range of filters (radiometric or spectrometric) and can be tuned to a particular wavelength. Thus the invention can be used for both detection and missile characterization of various engine plumes.

That is there are a number of chemical species associated with various engine plumes. These include aluminum, aluminum perchlorate, carbon dioxide, carbon monoxide, copper, copper hydride, hydrogen chloride, hydroxyl, methane, mono-methyl hydrazine, nitric acid, nitric oxide, nitrogen dioxide, nitrous oxide, polybutadiene, potassium, sodium, sulfur dioxide, and water.

An advantage of this invention over typical electro-optical passive sensors for early missile launch warning is that it is able to detect a missile launch when the missile launch area is obscured by clouds. Clouds may limit the effectiveness of typical sensors, which employ a wide band spectral filter. A new feature of this invention is that it employs a sensor with a narrow band spectral filter at a wavelength that is radiated through clouds.

By selecting a very narrow spectral range and at a wavelength where the water in clouds does not absorb the missile plume emissions, a sensor can detect a missile launch under cloud conditions.

More specifically, the present invention detects missile launches from an overhead surveillance platform. The invention is a passive electro-optical sensor which detects the narrow electromagnetic spectral emissions created in a rocket engine plume when a missile is launched. A unique feature of this invention is that it is able to detect the missile's spectral emissions through clouds. Typical early missile launch warning systems using passive electro-optical sensors do not see through clouds and will likely not detect a missile launch at the instant of rocket engine ignition if the missile launch area is obscured by clouds. The time from rocket engine ignition to passing through a cloud layer can be up to thirty seconds or more. This invention, therefore, has the capability to provide thirty seconds of additional warning time of a launch than typical systems during cloudy weather conditions. To demonstrate the invention the atomic line emission of sodium (present in rocket engine plumes) at 589.6 nanometers (nm) was used. As noted above, the invention is easily adaptable for other spectral emission lines which are scattered and transmitted through clouds.

The field demonstrations of the present invention thus included an aircraft mounted sensor and a sensor carried on-board an earth-orbiting satellite. The aircraft carried a narrow-band filtered radiometer. The satellite carried a spectrographic imager. However, either vehicle could have carried the other detector system. Both systems spectrally isolate the emission wavelength of interest and generate a radiometric measurement of the signal intensity. The aircraft and satellite sensors flew above a simulated rocket engine emission source at 589.6 nm and collected data. The collected data, data processing and analysis show this invention is capable of detecting the narrow spectral emissions associated with a missile launch. The advantages of this invention over typical early warning sensors are, it does not require cryogenic focal planes, does not require large optics, and can see a missile launch when the launch area is obscured by clouds.

What is claimed is:

1. A rocket plume detector comprising:
   a) a passive electro-optical sensor for detecting narrow band spectral emissions in a rocket engine plume, including through clouds and
   b) a lock-in amplifier to reduce background radiation for enhanced plume detection, said sensor being mounted on an above-flying or orbiting platform.

2. The detector of claim 1 wherein said sensor isolates the rocket plume wavelength of interest selected from the group of aluminum, aluminum perchlorate, carbon dioxide, carbon monoxide, copper, copper hydride, hydrogen chloride, hydroxyl, methane, mon-methyl hydrazine, nitric acid, nitric oxide, nitrogen dioxide, nitrous oxide, polybutadiene, potassium, sodium, sulfur dioxide, and water to detect a rocket launch plume.

3. The plume detector of claim 2 wherein said sensor can spectrally isolate or detect the emission wavelength of interest in the plume of a rocket being launched through fog, clouds and other water vapor.

4. The plume detector of claim 3 wherein said sensor can spectrally detect the emission wavelength of Na or K in a rocket engine plume.

5. The plume detector of claim 1 wherein said platform is an aircraft or an orbiting satellite.

6. The detector of claim 5 which includes a narrow band filtered radiometer when carried on said aircraft or includes a spectrographic imager when carried on said satellite or vice versa.

7. The plume detector of claim 5 employing ultraviolet and visible imagers and spectrographic imagers as a UVISI sensor on-board said satellite platform, to measure from space, a ground-based Na emission source or to measure from space, the emission of interest in the plume of a rocket being launched.

8. The plume detector of claim 5 employing a sensor with a narrow band spectral filter at a wavelength that is radiated through clouds.

9. The plume detector of claim 5 adapted to employ a plurality of filters, radiometric or spectrometric, which detector is tunable to a desired rocket plume emission wavelength.

10. The rocket plume detector of claim 9 being suited for both missile detection and characterization.

11. The detector of claim 1 wherein said sensor has
a) a narrow band filtered photometer,
b) data acquisition electronics and
c) a computer to monitor & record resulting data.

12. The plume detector of claim 1 comprising
a) collection optics for plume emissions,
b) a focal plane assembly which includes a spectral filter,
c) data acquisition avionics,
d) a global positioning system (GPS) receiver and
e) a computer for receiving the detector data signal and the GPS data for data acquisition, storage, processing and display.

13. The plume detector of claim 12 wherein said focal plane assembly includes a photomultiplier and said spectral filter serves to pass the emission of interest and to reject the background emission.

14. The plume detector of claim 12 wherein said GPS receiver records the flight path of the detector platform.

15. The plume detector of claim 12 wherein a 10-nm-wide or spectral filter suitable for nighttime emission detection is replaced with a 0.005 nm atomic line filter (ALF) for daytime emission detection.

16. A method of detecting a rocket plume comprising:
a) employing a passive electro-optical sensor for detecting narrow band spectral emissions in a rocket engine plume, including through clouds and
b) employing a lock-in amplifier to reduce background radiation for enhanced plume detection, said sensor being mounted on an above-flying or orbiting platform.

17. The method of claim 16 wherein said sensor isolates the rocket plume wavelength of interest selected from the group of aluminum, aluminum perchlorate, carbon dioxide, carbon monoxide, copper, copper hydride, hydrogen chloride, hydroxyl, methane, mon-methyl hydrazine, nitric acid, nitric oxide, nitrogen dioxide, nitrous oxide, polybutadiene, potassium, sodium, sulfur dioxide, and water to detect a rocket launch plume.

18. The method of claim 16 wherein said platform is an aircraft or an orbiting satellite.

19. The method of claim 16 wherein said sensor can spectrally isolate or detect the emission wavelength of interest in the plume of a rocket being launched through fog, clouds and other water vapor.

20. The method of claim 19 wherein said sensor can spectrally detect the emission wavelength of Na or K in a rocket engine plume.

21. The method of claim 18 employing a sensor with a narrow band spectral filter at a wavelength that is radiated through clouds.

* * * * *